United States Patent [19]

Abazajian

[11] Patent Number: 5,049,687
[45] Date of Patent: Sep. 17, 1991

[54] ETHYLENE CHAIN GROWTH PROCESS
[75] Inventor: Armen N. Abazajian, Houston, Tex.
[73] Assignee: Ethyl Corporation, Richmond, Va.
[21] Appl. No.: 601,405
[22] Filed: Oct. 22, 1990
[51] Int. Cl.$^5$ .............................................. C07F 5/06
[52] U.S. Cl. .................................... 556/190; 556/170; 556/187
[58] Field of Search ........................ 556/170, 187, 190
[56] References Cited

U.S. PATENT DOCUMENTS

| | | | |
|---|---|---|---|
| 4,544,762 | 10/1985 | Kaminsky et al. | 556/187 X |
| 4,730,072 | 3/1988 | Schoenthal et al. | 556/187 X |
| 4,732,992 | 3/1988 | Fannin et al. | 556/187 X |
| 4,908,463 | 3/1990 | Bottelberghe | 556/179 |
| 4,924,018 | 5/1990 | Bottelberghe | 556/179 |
| 4,948,906 | 8/1990 | Beard | 556/187 |
| 4,952,714 | 8/1990 | Wellburn, Jr. | 556/179 |

Primary Examiner—Arthur C. Prescott
Attorney, Agent, or Firm—David M. Bunnell

[57] ABSTRACT

An improved ethylene chain growth process in which ethylene and an alkyl aluminum compound are mixed and fed into an externally cooled, tubular coil reactor where said mixture is reacted at elevated temperature and pressure so as to form tri-$C_2$–$C_{20+}$ alkyl aluminum compounds the improvement comprising reducing the rate of reactor fouling by precooling the ethylene to a temperature of from about 30° to 70° C. prior to mixing it with the alkyl aluminum compound.

5 Claims, No Drawings

ETHYLENE CHAIN GROWTH PROCESS

BACKGROUND

This invention relates generally to the preparation of higher alkyl aluminum compounds by an ethylene chain growth process and more specifically to the reduction of reactor fouling of tubular reactors used in such process.

Alpha-olefins are made in commercial quantities by a process initially developed in the fifties by Karl Ziegler and his co-workers. The so-called Ziegler process involves a chain growth reaction of triethyl aluminum ("TEA") and ethylene at temperatures in the range of 200° F.–500° F. and pressures in the range of 2000–5000 psig to yield a mixture of tri-$C_{2-20+}$ alkyl aluminum having a Poisson alkyl distribution and $C_{2-20}$ olefins. The ethylene is flashed from the reaction mixture for recycle and the light olefins through decene-1 can be distilled from the mixed aluminum alkyls since they have a normal boiling point below the lightest aluminum alkyl (viz. TEA). The mixed aluminum alkyls can be subjected to a displacement reaction with an alpha-olefin such as ethylene to produce mainly triethylaluminum and a mixture of $C_2$ to $C_{30}$ or higher α-olefins. The lighter olefins are removed by distillation and the distillation bottoms including triethylaluminum and some mixed olefins can be recycled to the chain growth process.

Examples of patents which disclose variations of the ethylene chain growth process are U.S. Pat. No. 2,863,896; U.S. Pat. No. 2,889,385; U.S. Pat. No. 2,906,794; U.S. Pat. No. 2,971,969; U.S. Pat. No. 3,180,881; U.S. Pat. No. 3,210,435; U.S. Pat. No. 3,227,773; U.S. Pat. No. 3,278,633; U.S. Pat. No. 3,352,940; U.S. Pat. No. 3,358,050; U.S. Pat. No. 3,359,292; U.S. Pat. No. 3,384,651; U.S. Pat. No. 3,391,219; U.S. Pat. No. 3,415,861; U.S. Pat. No. 3,458,594; U.S. Pat. No. 3,487,097; U.S. Pat. No. 3,663,647; U.S. Pat. No. 3,789,091; U.S. Pat. No. 4,314,090 and U.S. Pat. No. 4,935,569 where teachings are incorporated herein by reference.

The preparation of higher trialkyl aluminum compounds from an alkyl aluminum having fewer carbon atoms, such as triethylaluminum, by the controlled chain growth reaction with ethylene is highly exothermic. In one commercial scale chain growth process, a tubular coil reactor is surrounded by one or more shells filled with a fluid heat exchange medium such as an organic liquid or water which is circulated to remove heat from the reaction such that the desired reaction temperature, usually from about 90° C. to 260° C., is maintained. The reactor temperature is chosen to be high enough to maintain a practical rate of reaction and yet not so high as to cause a significant amount of undesirable side reactions such as decomposition of the aluminum alkyls. A problem associated with such reactor systems is that ethylene polymer deposits build up on the reactor walls which eventually reduce the flow through the reactor. When such deposits become so severe as to inhibit practical operation, the reactor must be shut down and cleaned. I have now discovered an improved chain growth process which greatly extends the reactor life between cleanings.

BRIEF SUMMARY

In accordance with this invention there is provided an improved ethylene chain growth process in which ethylene and an alkyl aluminum compound are mixed and fed into an externally cooled, tubular coil reactor where the mixture is reacted at elevated temperature and pressure so as to form higher trialkyl aluminum compounds, the improvement comprising reducing the rate of reactor fouling by precooling the ethylene to a temperature of from about 30° C. to 70° C. prior to mixing it with the alkyl aluminum compound.

DETAILED DESCRIPTION

According to the chain growth process, ethylene and an alkyl aluminum such as triethylaluminum are fed to a chain growth reactor which is maintained under chain growth conditions. These conditions are a temperature in the range of about 90° C.–260° C. and, preferably, 120° C.–175° C. and pressures in the range of about 2000 to 5000 psig and, preferably, 2500 to 3500 psig. Residence time of ethylene and TEA in the chain growth reactor is selected to be long enough to increase the chain length of the alkyls bonded to aluminum to a mole average chain length of about 6–12 carbon atoms. Depending on temperature and pressure, a residence time on the order of 15 minutes to about 1 hour is usually satisfactory.

An example of a tubular chain growth reactor whose operation is improved by the process of the invention consists of two reactor shells operated in series. Each shell is a cylinder which contains a longitudinal coil of pipe having an inner diameter of 4". The coils are of sufficient length (about 3.5 miles) to provide the desired resistance time. Boiler feed water is fed to the shell side of the reactor where it is vaporized by the heat liberated from the growth reaction taking place inside the tubes. A heat exchanger is used to recover the heat from the steam and the condensed water is returned to the reactor shell.

The chain growth product from the reactor is sent to a displacement reactor where the higher alkyl groups are displaced by ethylene and recovered as $C_4$ to about $C_{30}$ α-olefin products. After separation of the product α-olefins by distillation, the bottoms stream, which is a mixture of triethylaluminum which contains some tributyl and trihexyl species and residual olefins, is recycled to the chain growth reactor where about 75 wt % of this recycle stream is mixed with a mixture of fresh and recycle ethylene and fed to the inlet of the reactor. The remaining 25 wt % of the ethylene feed is introduced at two points along the reactor tubes at about ⅓ (17%) and ⅔rds of the length of the reactor. Ethylene feed rates range from about 25,000–44,000 lb/hr at a temperature from about 90° C. to 120° C. and pressures of from about 2900–3000 psig. Alkyl aluminum feed rates range from about 28,500–52,000 lbs/hr at temperatures of from about 40° C.–50° C. and pressures of from about 2900–3100 psig. At a typical reactor operating pressure of about 3000 psig and a temperature of about 127° C., the reactor life is about 95 to 110 days before fouling causes the throughput to drop from an initial alkyl aluminum feed rate of 52,000 to about 28,500 lb/hr and the ethylene rates from 41,000 lb/hr to 25,000 lb/hr so that the reactor must be shut down and cleaned. Typical downtimes range from 72 to 168 hours. By cooling the ethylene according to the process of the invention, the rate of reactor tube fouling can be reduced by 25% to 50%.

According to a specific example of the improved process of the invention, the ethylene feed, after compression to operating pressure of about 3100 psig having a temperature of about 130° C. is sent to the inlet of a jacketed cooler where cooling water is about 30° C. is fed to the jacket at a rate such that the ethylene exiting from the cooler has a reduced temperature of about 65° C. The flow rate through the cooler can be adjusted to provide ethylene or temperatures of from about 30° C. to 70° C. The cooled ethylene at about 65° C. is then mixed with the alkyl aluminum and fed to the reactor. Using the same chain growth feed ratio and operating conditions as above (e.g. 3000 psig and 127° C.), reactor plugging rates are substantially reduced (25%-35% less) such that reactor life is extended to 125 to 150 days which significantly reduces production costs.

Although the process has been described with respect to an alkyl aluminum feed which is predominantly triethylaluminum, it should be recognized that it is applicable to chain growth processes starting with higher alkyl aluminums such as those having butyl, hexyl, octyl and decyl radicals and the like including mixtures thereof.

What is claimed is:

1. An improved ethylene chain growth process in which ethylene and an alkyl aluminum compound are mixed and fed into an externally cooled, tubular coil reactor where said mixture is reacted at elevated temperature and pressure so as to form higher trialkyl aluminum compounds, the improvement comprising reducing the rate of reactor fouling by precooling the ethylene to a temperature of from about 30° C. to 70° C. prior to mixing it with the alkyl aluminum compound.

2. The process of claim 1 wherein the alkyl aluminum compound is triethylaluminum.

3. The process of claim 1 wherein said elevated temperature and pressure are from about 90° C. to 260° C. and 2000 to 5000 psig.

4. The process of claim 3 wherein said elevated temperature and pressure are from about 120° C.–175° C. and 2500 to 3500 psig.

5. The process of claim 4 wherein said alkyl aluminum compound is triethylaluminum.

* * * * *

UNITED STATES PATENT AND TRADEMARK OFFICE
CERTIFICATE OF CORRECTION

PATENT NO. : 5,049,687
DATED : September 17, 1991
INVENTOR(S) : Armen N. Abazajian It is certified that error appears in the above-identified patent and that said Letters Patent is hereby corrected as shown below:

On the title page, item [56]:
Four cited U.S. references were omitted and should be entered, as follows:

| | | | |
|---|---|---|---|
| 2,863,896 | 12/1958 | Johnson | 556/190 |
| 2,889,385 | 6/1959 | Catterall et al. | 585/328 |
| 2,906,794 | 9/1959 | Aldridge et al. | 585/311 |
| 2,971,969 | 2/1961 | Lobo | 556/190 |

In the Claims, column 4, after line 20,

Claims 6 through 9 were omitted and should be entered, as follows:

6. The process of claim 1 wherein said alkylaluminum compound is a higher alkylaluminum compound.

7. The process of claim 9 wherein said higher alkylaluminum compound has alkyl radicals selected from the group consisting of butyl, hexyl, octyl and decyl including mixtures thereof.

8. The process of claim 4 wherein said alkylaluminum compound is a higher alkylaluminum compound.

UNITED STATES PATENT AND TRADEMARK OFFICE
CERTIFICATE OF CORRECTION

PATENT NO. : 5,049,687

DATED : September 17, 1991

INVENTOR(S) : Armen N. Abazajian

It is certified that error appears in the above-identified patent and that said Letters Patent is hereby corrected as shown below:

9. The process of claim 8 wherein said higher alkylaluminum compound has alkyl radicals selected from the group consisting of butyl, hexyl, octyl and decyl including mixtures thereof.

Signed and Sealed this

Second Day of March, 1993

Attest:

STEPHEN G. KUNIN

*Attesting Officer*  Acting Commissioner of Patents and Trademarks